United States Patent [19]

Müller et al.

[11]  4,250,336

[45]  Feb. 10, 1981

[54] PROCESS FOR THE MANUFACTURE OF RESORCINOLS FROM δ-KETOCARBOXYLIC ACID ESTERS

[75] Inventors: Werner H. Müller, Eppstein; Karl E. Mack, Kelkheim; Hansjörg Hey, Hofheim am Taunus, all of Fed. Rep. of Germany

[73] Assignee: Hoechst Aktiengesellschaft, Frankfurt am Main, Fed. Rep. of Germany

[21] Appl. No.: 45,941

[22] Filed: Jun. 6, 1979

[30] Foreign Application Priority Data

Jun. 8, 1978 [DE] Fed. Rep. of Germany ....... 2825073

[51] Int. Cl.$^3$ .............................................. C07C 37/00
[52] U.S. Cl. .................................................... 568/772
[58] Field of Search ......................................... 568/772

[56] References Cited

U.S. PATENT DOCUMENTS

| | | | |
|---|---|---|---|
| 3,950,438 | 4/1976 | Schaafsma et al. | 568/772 |
| 4,018,833 | 4/1977 | Müller et al. | 568/772 |
| 4,154,965 | 5/1979 | Meijer et al. | 568/772 |

FOREIGN PATENT DOCUMENTS

| | | | |
|---|---|---|---|
| 2412371 | 9/1974 | Fed. Rep. of Germany | 568/772 |
| 2450086 | 4/1976 | Fed. Rep. of Germany | 568/772 |
| 2533920 | 2/1977 | Fed. Rep. of Germany | 568/772 |

*Primary Examiner*—Werren B. Lone
*Attorney, Agent, or Firm*—Curtis, Morris & Safford

[57]  ABSTRACT

Resorcinols are prepared by converting δ-ketocarboxylic acid esters in the gaseous phase at a temperature from 250° to 500° C. in the presence of hydrogen at a catalyst. The catalyst consists of two components which are prepared separately and combined thereafter. The first component contains at least one compound of a metal of group VIII and/or at least one compound of a metal of group I B supported on one or several carrier materials. The second component contains at least one compound of a metal of group II A and/or IV A and/or III B and/or IV B supported on one or several carrier materials. A particularly preferred catalyst consists of a mixture of equal volume parts of platinum/charcoal as first component and of thorium/charcoal as second component.

13 Claims, No Drawings

PROCESS FOR THE MANUFACTURE OF RESORCINOLS FROM δ-KETOCARBOXYLIC ACID ESTERS

The present invention relates to a process for the manufacture of resorcinols by catalytic reaction of δ-ketocarboxylic acid esters in the gaseous phase in the presence of hydrogen.

Resorcinols are being used as synthetic resin components in the rubber and wood industry, as coupling components in diazotypy and as antiseptics.

It is known to prepare cyclohexane-1,3-diones by cyclization of δ-ketocarboxylic acid esters in the liquid phase using strong bases and to convert them thereafter into resorcinols by dehydrogenation in the liquid phase (cf. DE-OS No. 25 33 920). It is further known to prepare resorcinols by catalytic dehydrocyclization of δ-ketocarboxylic acids or lactones of the latter (cf. DE-OS No. 24 50 086) or of δ-ketocarboxylic acid esters (DE-OS No. 24 12 371) in the gaseous phase.

The profitability of a large-scale industrial process is improved substantially when this process can be carried out in a single step in the gaseous phase without yielding worthless, polluting by-products such as inorganic salts. A process of this type can be distinguished by a high selectivity of the reaction and a high conversion and, if noble metal catalysts are used, by a high yield relative to the quantity of noble metal, a long life or good regenerability.

The above-specified liquid phase process for the manufacture of resorcinols yielding as intermediates cyclohexane-1,3-diones, has the disadvantage of being a two-stage process and of proceeding with the formation of stoichiometrical quantities of inorganic salts. Both of the above-specified gaseous phase processes have relatively low conversion rates and relatively low yields, relative to the quantity of noble metal.

A process has now been found for the manufacture of resorcinols of the formula

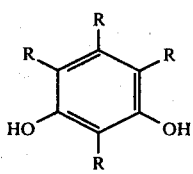

wherein the radicals R may be identical or different and, independent from one another, each are hydrogen, alkyl, cycloalkyl, aryl, alkoxy or carbalkoxy having altogether up to 12 carbon atoms, by reaction of a δ-ketocarboxylic acid ester of the formula

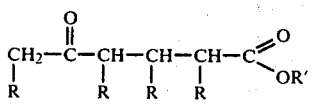

wherein R is defined as above and R' is alkyl, cycloalkyl or aryl having up to 8 carbon atoms, in the gaseous phase at a temperature of from 250° to 500° C. in the presence of hydrogen and a catalyst, wherein the catalyst comprises two components, the first component consisting of one or more carrier materials, onto which at least one compound of a metal of group VIII and/or at least one compound of a metal of group I B has been applied and the second component consisting of one or more carrier materials, onto which at least one compound of a metal of group II A and/or IV A and/or III B and/or IV B of the periodic system has been applied.

The catalyst therefore consists of two different components, the first component containing at least one element of the following class, hereafter designated as class I: iron, cobalt, nickel, copper, ruthenium, rhodium, palladium, silver, osmium, iridium, platinum, gold and the second component containing at least one element of the following class, hereafter designated as class II: beryllium, magnesium, calcium, strontium, barium, germanium, tin, lead, scandium, yttrium, lanthanum, lanthanides, titanium, zirconium, hafnium, thorium, uranium.

If the first component contains only one element of class I, this element may be applied onto one single carrier material or onto several different carrier materials. If the first component contains several elements of class I, all of them may be applied onto one single carrier material or alternatively several different carrier materials may be used, onto each of which one or several of the corresponding elements are applied.

The same applies to the application of one or several elements of class II onto a carrier material in order to provide the second component. For the second component there may be used the same carrier material as in the first component or several carrier materials identical to those in the first component or alternatively, one or more carrier materials different from those in the first component may be used.

It is essential to prepare both catalyst components separately and to combine them thereafter to provide the catalyst according to the invention. A catalyst of this type consisting of two separately prepared components is superior over catalysts containing elements of the classes I and II applied onto the same catalyst particles in that it has a longer life and a better reproducibility of the activity.

In the process of the invention the conversion rate of δ-ketocarboxylic acid esters and the yield of resorcinol, relative to the noble metal quantity, are by far higher than in both of the above-specified gaseous phase processes. The reaction pressure is not critical, generally it is operated under normal pressure, however, elevated pressure or reduced pressure may be applied alternatively. A pressure range from 0.1 to 10 bars is particularly advantageous. The reaction temperature ranges preferably from 300° to 400° C.

The radicals R in the δ-ketocarboxylic acid ester may be branched or straight chained alkyls such as methyl, ethyl, propyl, butyl, pentyl, hexyl, octyl, decyl and dodecyl. As cycloalkyl groups cyclopentyl, cyclohexyl, cyclodecyl and cyclododecyl may be mentioned. Alkyl groups or cycloalkyl groups having up to 6 carbon atoms are used preferably. Suitable aryl radicals are phenyl and naphthyl. Advantageously, at least two radicals R of the starting compound and particularly advantageously all of the radicals R should denote hydrogen.

If one of the radicals R is alkoxy or carbalkoxy, the other radicals R are preferably hydrogen. The alkyl radical of alkoxy or carbalkoxy preferably is methyl, ethyl, n-propyl or n-butyl.

The radical R' preferably is straight chained alkyl or aryl such as benzyl, tolyl, phenyl; particularly advantageously R' is methyl ethyl, n-propyl and n-butyl.

As starting compound of the process of the invention there is used preferably the methyl, ethyl or n-butyl ester of δ-ketohexanoic acid or the methyl ester of the following acids: δ-ketoheptanoic acid, γ-(n-hexyl)-δ-ketohexanoic acid, β-(n-pentyl)-δ-ketohexanoic acid, β-carbomethoxy-δ-ketohexanoic acid, γ-methoxy-δ-ketohexanoic acid and α-methyl-β-methyl-δ-ketohexanoic acid.

Preferred elements of class I that are applied onto the carrier material in the form of compounds are platinum, palladium, iridium, rhodium, ruthenium and osmium. Palladium and platinum and in particular platinum are the most preferred elements because of their great efficiency. The proportion by weight of the element(s) of class I, calculated as metal, relative to the total weight of the first catalyst component, ranges from 0.01 to 10 weight %, preferably from 0.1 to 3 weight %.

Preferred elements of class II applied onto the carrier material in the form of compounds, are magnesium, calcium, strontium, tin, lead, zirconium, scandium, lanthanum, the lanthanides, thorium and uranium, of these strontium, tin, zirconium and thorium, in particular thorium, are used preferably because of their high efficiency.

The proportion by weight of the element(s) of class II, calculated as metal, relative to the total weight of the second catalyst component, ranges from 0.05 to 10, preferably from 0.5 to 4, weight %.

Preferred combinations of elements of class I and class II are palladium/zirconium, platinum/zirconium, palladium/platinum/tin, palladium/platinum/strontium, platinum/iridium/thorium, palladium/thorium, palladium/platinum/thorium, platinum/thorium, the combinations platinum/thorium, palladium/thorium and palladium/platinum/thorium, in particular platinum/thorium, being used preferably.

Suitable carrier materials in both catalyst components are charcoal, silicon dioxide, silicic acid, or the corresponding gels, clays, silicates, chamotte, aluminum, chromium oxide, zinc oxide, magnesium oxide, zirconium dioxide, boric acid, aluminum oxide and mixed oxides thereof, alumosilicates, spinels and zeolites. Charcoal, aluminum oxide, silicon dioxide, and aluminum oxide-chromium oxide, in particular charcoal, are the preferred carrier materials.

The catalyst of the present invention consists of 2 components which are mixed with one another generally and fed subsequently to a reaction tube in such a way that either one single zone or several zones separated from one another are formed. The particle distribution of both components in the mixture need not necessarily be uniform and likewise the particle distribution of both components in the reaction tube need not necessarily be uniform and regular. Preferably, however, a mixture having a uniform distribution of both components is used and this mixture is preferably fed to the reaction tube in a way such that it forms one single zone which has a uniform particle distribution of both components.

The volume ratio of both catalyst components of the mixture should be from 95:5 to 5:95, preferably from 90:10 to 10:90, a ratio of 75:25 to 25:75 and in particular of 50:50 is most preferred.

The following mixtures consisting of identical volume parts of each component constitute catalysts of particularly high activity:

| first component: | second component: |
| --- | --- |
| palladium/platinum on $Al_2O_3$—$Cr_2O_3$ | strontium on charcoal |
| platinum/iridium on $Al_2O_3$ | thorium on $Al_2O_3$ |
| palladium on $Al_2O_3$—$Cr_2O_3$ | thorium on charcoal |
| palladium/platinum on charcoal | zirconium on charcoal |
| palladium/platinum/iridium on charcoal | thorium on charcoal |
| platinum on charcoal | thorium on charcoal |

A mixture of identical volume parts of platinum on charcoal combined with thorium on charcoal constitutes a particularly preferred catalyst.

The use of the above-specified catalyst makes it possible to convert δ-ketocarboxylic acid esters with a high conversion rate and a good selectivity into resorcinols with simultaneously high yield, relative to the noble metal quantity. As an example, resorcinol may be prepared from δ-ketohexanoic acid methyl ester with a yield from 80 to 100 g of resorcinol per gram of noble metal, a selectivity from 75 to 85% and a conversion rate from 85 to 90% of the ester.

If required, the catalysts may be regenerated repeatedly, for example by passing over them in the reaction tube a gas mixture consisting of oxygen and a further gas such as nitrogen, carbon dioxide, steam or a noble gas. In this process the temperature of the catalyst, depending on the nature of the carrier material, is kept between 100° to 500° C., preferably between 250° and 400° C. The oxygen content of the gas mixture is generally in the range of from 0.5 to 10 volume %, preferably from 1 to 5 volume %. A mixture of air and nitrogen is particularly convenient. After several hours of treatment with the described gas the catalyst is treated with a mixture of hydrogen and another gas such as nitrogen, carbon dioxide, steam or a noble gas, for example at a temperature from 100° to 400° C., this treatment regenerates the catalyst to substantially its original activity. The reaction mixture consisting of $H_2$/ketoester is likewise suitable.

Both catalyst components are prepared in the following manner:

At least one compound of an element of class I or of class II, respectively, is applied onto the corresponding carrier by any of the usual impregnation methods. When several compounds of elements of the same class are applied onto one carrier, this may be done simultaneously or subsequently. Difficultly soluble compounds may be dissolved in an excess of solvent. In this case the carrier material is suspended in the solution and the excess solvent is evaporated or impregnation is repeated several times. Compounds that are difficultly soluble in water may be brought into a water-soluble form by adding other substances, for example, in the case of palladium chloride, sodium chloride. These additives need not necessarily be removed upon impregnation. Suitable compounds of elements of class I are for example those that derive from nitrogen-containing acids, for example nitrates, nitrites, cyanides and rhodanides or complex compounds with nitrogen-containing ligands such as ammonia or cyanide. Furthermore there may be used sulfates, chlorides, bromides or halogen-containing complex compounds or carboxylates such as acetates, oxalates or tartrates, or organic compounds derived from CH acids such as acetylacetone. Preferred compounds are palladium dinitrate, platinum dicyanide, potassium hexacyanoplatinate, potassium tetracyanoplatinate, potassium tetranitroplatinate, tetrammine palladium dichloride, palladium dichloride, palladium sulfate, platinum tetrachloride, hexachloroplatinic acid, potassium hexachloroplatinate, sodium tetrachloroplatinate, potassium hexabromoplatinate, palladium or platinum diacetate, palladium or platinum acetylacetonate. Hexachloroplatinic acid, potassium hexachloroplatinate, potassium tetracyanoplatinate, palladium diacetate and platinum diacetate are the most preferred compounds.

Suitable compounds of elements of class II are, by way of example, nitrates, nitrites, halides, sulfates, carbonates, acetates and oxalates. Nitrates, halides or oxalates are used preferably.

Suitable solvents for compounds of the elements of class I as well as for compounds of the elements of class II are water or organic solvents such as alcohols, ketones, nitriles, carboxylic acid esters and halogenated hydrocarbons. Methanol, acetone, methylene chloride, chloroform and mixtures of these compounds or water or mixtures of water and acetone or of water and methanol are used preferably.

The process of the invention is carried out in the following manner:

The gaseous starting compound in admixture with hydrogen is passed over the catalyst at a molar ratio from 1:1 to 50:1, preferably from 3:1 to 15:1.

In addition to hydrogen gases such as nitrogen, noble gas, carbon dioxide or steam may be present with nitrogen in combination with hydrogen at a ratio of $H_2:H_2$ of 4:1 to 1:4, being the preferred additional gas.

The following mode of operation has proven particularly advantageous for carrying out the process of the invention: The δ-ketocarboxylic acid ester is converted in a vertically arranged, electrically heatable reaction tube in the central part of which the catalyst is placed.

The starting compound is introduced into an evaporator, mixed with hydrogen or a mixture of hydrogen and nitrogen, for example, and passed over the catalyst. Operation is carried out under normal pressure, since the pressure is not critical for the reaction. At the end of the reaction tube, the reaction mixture is condensed. The resorcinol formed may be isolated either by distillation or by extraction.

The following examples illustrate the invention:

COMPARATIVE EXAMPLE 1

Two comparative catalysts A and B are prepared using as carrier material granular charcoal. Catalyst A is prepared by impregnation with an aqueous solution containing hexachloroplatinic acid and palladium dichloride dissolved with the aid of sodium chloride and catalyst B is prepared by impregnation with an aqueous solution of hexachloroplatinic acid and palladium dichloride dissolved by help of hydrochloric acid. The catalysts are dried for three hours at 100° C. under 0.1 bar.

Catalyst A contains 2.4 weight % of palladium, 0.6 weight % of platinum, 4 weight % of sodium chloride and catalyst B contains 1.6 weight % of palladium and 0.5 weight % of platinum.

A mixture of 20 Nl/h (Nl=normal liters are calculated under normal conditions of temperature and pressure) of hydrogen, 14 Nl/h of nitrogen and 3.2 Nl/h of gaseous δ-ketohexanoic acid methyl ester is passed from the top over a 70 ml portion of catalyst A or B, respectively, placed in a vertically arranged, electrically heated reaction tube, and which have been treated immediately prior to use for 3 hours at 320° C. with a gas mixture of 20 Nl/h of $H_2$ and of 14 Nl/h of $N_2$. The reaction product is condensed and analyzed by gas chromatography.

The conversion rates of δ-ketohexanoic acid methyl ester and the selectivities of the resorcinol formation during the test duration of 75 hours are listed in Table 1.

TABLE 1

| Test duration (hours) | 15 | | 30 | | 45 | | 60 | | 75 | |
|---|---|---|---|---|---|---|---|---|---|---|
| catalyst | A | B | A | B | A | B | A | B | A | B |
| % Conversion rate | 25 | 30 | 40 | 35 | 35 | 38 | 22 | 27 | 8 | 15 |
| % Selectivity (resorcinol) | 35 | 28 | 55 | 58 | 62 | 54 | 41 | 32 | 27 | 19 |

COMPARATIVE EXAMPLE 2

Two catalysts C and D are prepared which have the same composition as catalyst A of Comparative Example 1, except that they contain additionally 2 weight % of thorium. Catalyst C is prepared in the following manner: Thorium is applied onto granular charcoal as aqueous thorium nitrate solution, followed by calcination upon a 4 hours' drying at 100° C. under 0.1 bar in a nitrogen current. Next, palladium and platinum are applied in analogous manner as in the case of catalyst A. For preparing catalyst D, there is used a catalyst that has been prepared in the same manner as catalyst A of Comparative Example 1 and which has been treated for 3 hours at 320° C. with 20 Nl/h of $H_2$ and 14 Nl/h of $N_2$ and which is then impregnated with an aqueous thorium nitrate solution and dried thereafter at 100° C. under 0.1 bar.

Catalyst C or D, respectively, are used under the same conditions as in Comparative Example 1, however for a longer test duration.

The conversion rates of δ-ketohexanoic acid methyl ester and the selectivities of the formation of resorcinol during a test duration of 210 hours are listed in Table 2.

TABLE 2

| Test duration (hours) | 30 | | 60 | | 90 | | 130 | | 170 | | 210 | |
|---|---|---|---|---|---|---|---|---|---|---|---|---|
| catalyst | C | D | C | D | C | D | C | D | C | D | C | D |
| % Conversion rate | 55 | 52 | 60 | 55 | 62 | 57 | 61 | 56 | 58 | 53 | 57 | 50 |
| % Selectivity (resorcinol) | 55 | 47 | 58 | 54 | 57 | 52 | 52 | 46 | 44 | 39 | 38 | 38 |

It can be clearly seen from this Example that the conversion rate of the reaction and the life of the catalyst are notably improved by the addition of thorium.

EXAMPLE 1

Catalyst E is prepared which consists of two catalyst components. The first of these components is prepared as catalyst A of Comparative Example 1. It contains 2.4 weight % of palladium, 0.6 weight % of platinum and 4 weight % of sodium chloride. The second component contains 2 weight % of thorium and is prepared by impregnation of granular charcoal with an aqueous solution of thorium nitrate, drying at 100° C. in vacuo and calcination at 400° C. in a nitrogen current for 4 hours. A 35 ml portion of both components is mixed intimately and the resulting mixture is fed to the reaction tube.

Catalyst E is treated for 3 hours at 330° C. with 30 normal liters/h of a mixture of nitrogen and hydrogen at a ratio of 2:3. Next, at 340° to 345° C. 20 normal liters of hydrogen, 14 normal liters of nitrogen and 3.2 normal liters of gaseous δ-ketohexanoic acid methyl ester per hour are passed over the catalyst.

The conversion rates of δ-ketohexanoic acid methyl ester and the selectivities of the resorcinol formation during a test duration of 480 hours are listed in Table 3.

TABLE 3

| Test duration (hours) | 48 | 72 | 144 | 288 | 384 | 480 |
|---|---|---|---|---|---|---|
| % Conversion rate | 96 | 94 | 93 | 85 | 76 | 68 |
| % Selectivity (resorcinol) | 66 | 68 | 72 | 71 | 68 | 64 |

It can be clearly seen from this Example that the conversion rate, the selectivity of the reaction and life of the catalyst are improved notably by mixing catalyst A with a thorium-containing further catalyst component.

EXAMPLE 2

The catalyst used in Example 1 is regenerated after a test duration of 480 hours. For this purpose a mixture of 6 normal liters of air and 80 normal liters of nitrogen per hour is passed over the catalyst in the reactor while maintaining the temperature at 350° C. After 6 hours, 20 normal liters of hydrogen and 14 normal liters of nitrogen per hour are passed over the catalyst for a further 3 hours, then the reaction proceeds as in Example 1. The regeneration is repeated after a test duration of 720 hours. The results are listed in Table 4.

TABLE 4

| Test duration (hours) | 480 | regeneration | 576 | 672 | 720 | Regeneration | 816 | 912 | 960 |
|---|---|---|---|---|---|---|---|---|---|
| % Conversion rate | 68 | | 95 | 85 | 72 | | 91 | 82 | 65 |
| % Selectivity (resorcinol) | 64 | | 65 | 68 | 59 | | 64 | 65 | 52 |

EXAMPLE 3

Two catalyst components X and Y are prepared, X being identical to catalyst A of Comparative Example 1 and Y being prepared successively by impregnation of granular charcoal with an aqueous solution of thorium oxalate and ammonium oxalate at a ratio of 1:2.3 and by drying and calcination as described in Example 1. Hence, Y contains 2 weight % of thorium supported on charcoal and X contains 2.4% of palladium, 0.6% of platinum and 4% of sodium chloride. The two catalysts F and G are prepared from the components X and Y in the following manner:

F: Five minutes each of which having 15 ml are prepared from 25 ml of X and from 50 ml of Y at the following ratios
1. Y:X=3:3
2. Y:X=3.5:2.5
3. Y:X=4:2
4. Y:X=4.1:1.5
5. Y:X=5:1.

These five mixtures are subsequently fed to a reaction tube to form five zones.

G. Five mixtures each of which having a volume of 15 ml are prepared from 50 ml of X and from 25 ml of Y at the following ratios:
1. Y:X=3:3
2. Y:X=2.5:3.5
3. Y:X=2:4
4. Y:X=1.5:4.5 and
5. Y:X=1:5.

These five mixtures are again fed to a reaction tube successively to form five zones.

Catalyst F or G respectively is used as catalyst E of Example 1. The results are listed in Table 5.

TABLE 5

| Test duration (hours) | 48 | | 72 | | 144 | | 216 | | 288 | |
|---|---|---|---|---|---|---|---|---|---|---|
| catalyst | F | G | F | G | F | G | F | G | F | G |
| % Conversion rate | 88 | 92 | 86 | 90 | 82 | 90 | 74 | 86 | 68 | 82 |
| % Selectivity (resorcinol) | 55 | 58 | 62 | 65 | 66 | 66 | 63 | 64 | 59 | 60 |

It can be clearly seen from this Example that the catalyst components may be used at various volume ratios and that the catalyst may consist of several zones of different composition.

EXAMPLE 4

Four catalyst components are prepared analogously to the manufacture of the second component of Example 1, except that they contain instead of thorium 2 weight % of calcium, strontium, zirconium or tin, respectively, supported on charcoal. A 35 ml portion of each catalyst component is mixed each time with a 35 ml portion of a component prepared analogously to catalyst A in Comparative Example 1 and the mixtures are used in the conversion of the δ-ketohexanoic acid methyl ester analogously to catalyst E of Example 1, however, at different temperatures. The conversion rates obtained and the selectivities of the resorcinol formation are summarized in Table 6.

TABLE 6

| Test duration (hours) | | 72 | | 144 | |
|---|---|---|---|---|---|
| Element | Temperature °C. | % conversion rate | % Selectivity (resorcinol) | % conversion rate | % Selectivity (resorcinol) |
| Calcium | 320 | 82 | 56 | 71 | 52 |
| Strontium | 310 | 86 | 62 | 76 | 54 |
| Zirconium | 340 | 92 | 64 | 88 | 62 |
| Tin | 350 | 86 | 58 | 78 | 55 |

It can be clearly seen from this Example that the metals used display a similarity good action as compared to thorium, although thorium is the preferred metal (cf. Example 1).

EXAMPLE 5

Four catalyst components are prepared, each of which contains 2 weight % of thorium supported on different carriers, in the following manner:

Aluminum oxide (100 m$^2$/g), silicon dioxide (120 m$^2$/g), silica gel (350 m$^2$/g) or chromium oxide-aluminum oxide (60 m$^2$/g), respectively, are impregnated with aqueous thorium nitrate solution, dried at 100° C. under 0.1 bar and subsequently calcined for 4 hours at 400° C. A 35 ml portion of each component is mixed each time with a 35 ml portion of fresh catalyst A (cf. Comparative Example 1) and the mixtures are used under the conditions of Example 1 in order to convert the δ-ketohexanoic acid methyl ester. The conversion rates and the selectivities of the resorcinol formation are summarized in Table 7.

TABLE 7

| Test duration (hours) Carrier | 72 % Conversion rate | 72 % Selectivity (resorcinol) | 144 % Conversion rate | 144 % Selectivity (resorcinol) |
|---|---|---|---|---|
| Al$_2$O$_3$ | 82 | 55 | 68 | 46 |
| SiO$_2$ | 80 | 58 | 62 | 52 |
| SiO$_2$—gel | 88 | 61 | 79 | 55 |
| Cr$_2$O$_3$—Al$_2$O$_3$ | 86 | 56 | 72 | 48 |

EXAMPLE 6

Four catalyst components are prepared each of which contains 1.2 weight % of palladium and 0.3 weight % of platinum supported on aluminum oxide (100 m$^2$/g), silicon dioxide (120 m$^2$/g), silica gel (350 m$^2$/g) or chromium oxide-aluminum oxide (60 m$^2$/g), respectively, by impregnation of the carrier materials with a chloroform solution of palladium and platinum acetate and by subsequent drying at 100° C.

A 35 ml portion of each catalyst component is mixed each time with a 35 ml portion of a second catalyst component containing 2 weight % of thorium supported on charcoal and the mixtures are used analogously to Example 1.

The conversion rates and the selectivities of the resorcinol formation of summarized in Table 8.

TABLE 8

| Test duration (hours) Carrier | 72 % Conversion rate | 72 % Selectivity (resorcinol) | 144 % Conversion rate | 144 % Selectivity (resorcinol) |
|---|---|---|---|---|
| Al$_2$O$_3$ | 76 | 62 | 74 | 53 |
| SiO$_2$ | 68 | 58 | 58 | 43 |
| SiO$_2$—gel | 66 | 52 | 62 | 46 |
| Cr$_2$O$_3$—Al$_2$O$_3$ | 96 | 83 | 92 | 79 |

EXAMPLE 7

Six catalyst are prepared by mixing each time identical volume parts of two catalyst components. The proportion by weight of noble metal (iridium, platinum, palladium) of component I and the proportion by weight of thorium or zirconium, respectively, relative to the weight of component II, the carrier materials used in each case and the metal compound used for the manufacture of the components can be seen from Table 9. Each catalyst component is prepared with the use of water as solvent. Each of the compounds used as component I or II dried for 3 hours at 100° C. under 0.1 bar. Each of the compounds used as component II is calcined additionally for 4 hours at 400° C. in a nitrogen current. The catalyst obtained upon mixing the corresponding components I and II are used for reacting the δ-ketohexanoic acid methyl ester under the conditions of Example 1.

The conversion rates of δ-ketohexanoic acid methyl ester and the selectivities of the resorcinol formation during the test duration of 280 hours are likewise listed in Table 9.

TABLE 9

| Component I % Metal | Component I Carrier material | Component I Metal compound for carrier impregnation | Component II % Metal | Component II Carrier material | Component II Metal compound for carrier impregnation | Conversion % | Select. % |
|---|---|---|---|---|---|---|---|
| 0.3 Ir | charcoal | H$_2$IrCl$_6$ | 1 Th | charcoal | Th(NO$_3$)$_4$ | 62 | 72 |
| 0.5 Pt | " | H$_2$PtCl$_6$ | 2 Zr | SiO$_2$-gel | Th(NO$_3$)$_4$ | 78 | 68 |
| 0.3 Ir | " | H$_2$IrCl$_6$ | | | | | |
| 0.3 Pt | " | K$_2$Pt(CN)$_4$ | 1.5 Th | charcoal | Th(NO$_3$)$_4$ | 92 | 86 |
| 0.6 Pt | " | K$_2$PtCl$_6$ | 2 Th | " | Th(NO$_3$)$_4$ | 87 | 84 |
| 0.4 Pt | " | KCl + H$_2$PtCl$_6$ | 2 Th | " | Th(NO$_3$)$_4$ | 88 | 78 |
| 0.4 Pt | " | K$_2$PtCl$_6$ | 1 Th | " | Th(oxalate)$_2$ | 77 | 74 |
| 0.7 Pd | " | NaCl + PdCl$_2$ | | | | | |

EXAMPLE 8

A catalyst is prepared consisting of a mixture of equal volume parts of a component I (0.3 weight % of platinum supported on chromium oxide-aluminum oxide) and a component II (2 weight % of thorium supported on granular charcoal), platinum having been applied onto the carrier as platinum acetate in chloroform and thorium having been applied in the form of thorium nitrate in water.

A 70 ml portion of the resulting catalyst is used in the reaction of δ-ketohexanoic acid methyl ester at 350° C. after having been treated for 3 hours with a gas mixture of 20 Nl/h of hydrogen and 14 Nl/h of nitrogen at 325° C. 20 g δ-ketohexanoic acid methyl ester are evaporated per hour, mixed with 30 Nl of hydrogen and 20 Nl of nitrogen per hour and passed subsequently over the catalyst. During the test duration of 450 hours there are obtained 8865 g of condensate, from which resorcinol is formed by crystallization. Analysis by way of gas chromatography gives the following composition of the condensate:

| | | | | |
|---|---|---|---|---|
| resorcinol | 5265 | g = | 59.4 | weight % |
| δ-ketohexanoic acid methyl ester | 900 | g = | 10.15 | weight % |
| methanol | 1557 | g = | 17.56 | weight % |
| phenol | 225 | g = | 2.53 | weight % |
| cyclohexanone | 153 | g = | 1.72 | weight % |
| hexanoic acid methyl ester | 139 | g = | 1.57 | weight % |
| methyl propyl ketone | 122 | g = | 1.37 | weight % |
| cyclohexanedione-1,3 | 85.5 | g = | 0.97 | weight % |
| δ-caprolactone | 86 | g = | 0.98 | weight % |
| 3-methoxy-cyclohexene-2-one | 67 | g = | 0.76 | weight % |
| resorcinol monomethyl ester | 58 | g = | 0.66 | weight % |

The mixture further contains 1.6 weight % of water.

The resorcinol formation shows a selectivity of 85% and the conversion rate of δ-ketohexanoic acid methyl ester is 90%.

The catalyst is regenerated as described in Example 2 and used subsequently for a further 300 hours for the reaction. The selectivity of the resorcinol formation during this period of time is 81% and the conversion rate of δ-ketohexanoic acid methyl ester 88%. After repeated regenerations and a test duration of a further 300 hours, the selectivity is 74% and the conversion rate 84%.

What is claimed is:

1. Process for the manufacture of resorcinols of the formula

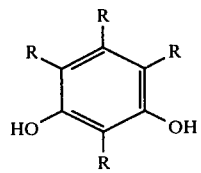

wherein the radicals R may be identical or different and, independent from one another, each are hydrogen, alkyl, cycloalkyl, aryl, alkoxy or carbalkoxy having altogether up to 12 carbon atoms, which comprises reacting a δ-ketocarboxylic acid ester of the formula

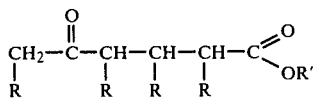

wherein R is defined as above and R' is alkyl, cycloalkyl or aryl of up to 8 carbon atoms, in the gaseous phase at a temperature of from 250° to 500° C. in the presence of hydrogen and a two-component catalyst, the first component consisting of one or more carrier materials containing at least one compound of a metal selected from the group consisting of Groups VIII and IB and the second component consisting of one or more carrier materials containing at least one compound of a metal of Groups II A, IV A, III B and IV B of the periodic system.

2. Process as defined in claim 1 wherein the first component contains at least one compound of platinum, palladium, iridium, rhodium, ruthenium or osmium and wherein the proportion by weight of the corresponding element, calculated as metal, relative to the total weight of the first component is in the range from 0.01 to 10 weight %.

3. Process as defined in claim 1 wherein the first component contains at least one compound of platinum or palladium.

4. Process as defined in claim 1 wherein the first component contains at least one compound of platinum.

5. Process as defined in claim 1 wherein the second component contains at least one compound of magnesium, calcium, strontium, tin, lead, zirconium, scandium, lanthanum, lanthanides, thorium or uranium and wherein the proportion by weight of the corresponding element, calculated as metal, relative to the total weight of the second component is in the range from 0.5 to 10 weight %.

6. Process as defined in claim 1 wherein the second compound contains at least one compound of strontium, tin, zirconium or thorium.

7. Process as defined in claim 1 wherein the second component contains at least one compound of thorium.

8. Process as defined in claim 1 wherein the two catalyst components are in the form of a uniform mixture.

9. Process as defined in claim 8, wherein the volume ratio of the first and second catalyst components is in the range of from 95:5 to 5:95.

10. Process as defined in claim 8 wherein the volume ratio is in the range from 90:10 to 10:90.

11. Process as defined in claim 8 wherein the volume ratio is in the range from 75:25 to 25:75.

12. Process as defined in claim 1 wherein the carrier materials of the catalyst are selected from the group consisting of charcoal, aluminum oxide, silicon dioxide and aluminum oxide-chromium oxide.

13. Process as defined in claim 1 wherein the carrier material is charcoal.

* * * * *

UNITED STATES PATENT AND TRADEMARK OFFICE
CERTIFICATE OF CORRECTION

PATENT NO. : 4,250,336
DATED : February 10, 1981
INVENTOR(S) : Muller et al.

It is certified that error appears in the above-identified patent and that said Letters Patent are hereby corrected as shown below:

Column 12, line 29 (claim 5), "0.5" should read --0.05--.

Signed and Sealed this

Nineteenth Day of May 1981

[SEAL]

Attest:

RENE D. TEGTMEYER

Attesting Officer

Acting Commissioner of Patents and Trademarks